US008323216B2

(12) United States Patent  (10) Patent No.: US 8,323,216 B2
Fabian  (45) Date of Patent: Dec. 4, 2012

(54) SYSTEM AND METHOD FOR APPLIED KINESIOLOGY FEEDBACK

(76) Inventor: William Fabian, Washington, DC (US)

( * ) Notice: Subject to any disclaimer, the term of this patent is extended or adjusted under 35 U.S.C. 154(b) by 302 days.

(21) Appl. No.: 12/687,634

(22) Filed: Jan. 14, 2010

(65) Prior Publication Data

US 2011/0077546 A1  Mar. 31, 2011

Related U.S. Application Data

(60) Provisional application No. 61/277,706, filed on Sep. 29, 2009.

(51) Int. Cl.
*A61B 5/00* (2006.01)
(52) U.S. Cl. ........................................................ 600/587
(58) Field of Classification Search .................. 600/587, 600/558
See application file for complete search history.

(56) References Cited

U.S. PATENT DOCUMENTS

| | | | |
|---|---|---|---|
| 5,187,506 A | 2/1993 | Carter | |
| 6,852,086 B2 * | 2/2005 | Atlas et al. | 600/595 |
| 6,854,879 B2 * | 2/2005 | Pavlidis | 374/45 |
| 7,938,785 B2 * | 5/2011 | Aguilar et al. | 600/558 |
| 2001/0028309 A1 * | 10/2001 | Torch | 340/575 |
| 2003/0133597 A1 * | 7/2003 | Moore et al. | 382/115 |
| 2003/0220550 A1 | 11/2003 | McCulloch et al. | |
| 2005/0124851 A1 | 6/2005 | Patton et al. | |
| 2005/0143629 A1 * | 6/2005 | Farwell | 600/300 |
| 2005/0165327 A1 | 7/2005 | Thibault et al. | |
| 2007/0066916 A1 | 3/2007 | Lemos | |
| 2008/0033252 A1 | 2/2008 | Estrella | |
| 2009/0216092 A1 * | 8/2009 | Waldorf et al. | 600/301 |

\* cited by examiner

*Primary Examiner* — Max Hindenburg
(74) *Attorney, Agent, or Firm* — Duane Morris LLP (57) ABSTRACT

Applied kinesiology method and device utilizes an examiner's autonomic response to truth/false or beneficial/non-beneficial stimulus and provides immediate feedback to the examiner in the context of an applied kinesiology exam. Kinesiology glasses detect local pupillary response to truthfulness locally and remotely. Through measurements of the pupils dilation or constriction and processing of the measurements, the response is obtained and feedback, via sensory stimulation, is provided to the examiner that reflects the pupillary response. The device and method effectively eliminate the subjective components of prior art muscle testing response from the hands of the testing examiner.

22 Claims, 7 Drawing Sheets

SYSTEM AND METHOD FOR APPLIED KINESIOLOGY FEEDBACK

CROSS REFERENCES

This application is a non-provisional application and claims priority benefit of co-pending provisional application Ser. No. 61/277,706 entitled "System and Method for Applied Kinesiology Feedback" filed Sep. 29, 2009. The entirety of which is hereby incorporated by reference.

BACKGROUND

The background of applied kinesiology (AK) in general dates back to George Goodhart, D. C. (1964) in which the observation that the gross, striated muscle response is one of going weak to a detrimental stimulus and remaining strong to a beneficial stimulus was made.

Applied kinesiology interactive assessment procedures represent a form of functional biomechanical and functional neurologic evaluation. The term "functional biomechanics" refers to the clinical assessment of posture, organized motion such as in gait, and ranges of motion. Muscle testing readily enters into the assessment of postural distortion, gait impairment and altered range of motion. During a functional neurologic evaluation, muscle tests are used to monitor the physiologic response to a physical, chemical or mental stimulus. The observed response is correlated with clinical history and physical exam findings and, as indicated, with laboratory tests and any other appropriate standard diagnostic methods.

The applied kinesiology response has been used by chiropractors since the mid 20th Century for diagnostic purposes. In the past, the muscle response measure was achieved through gross physical movements of voluntary muscle groups.

Figure 1:
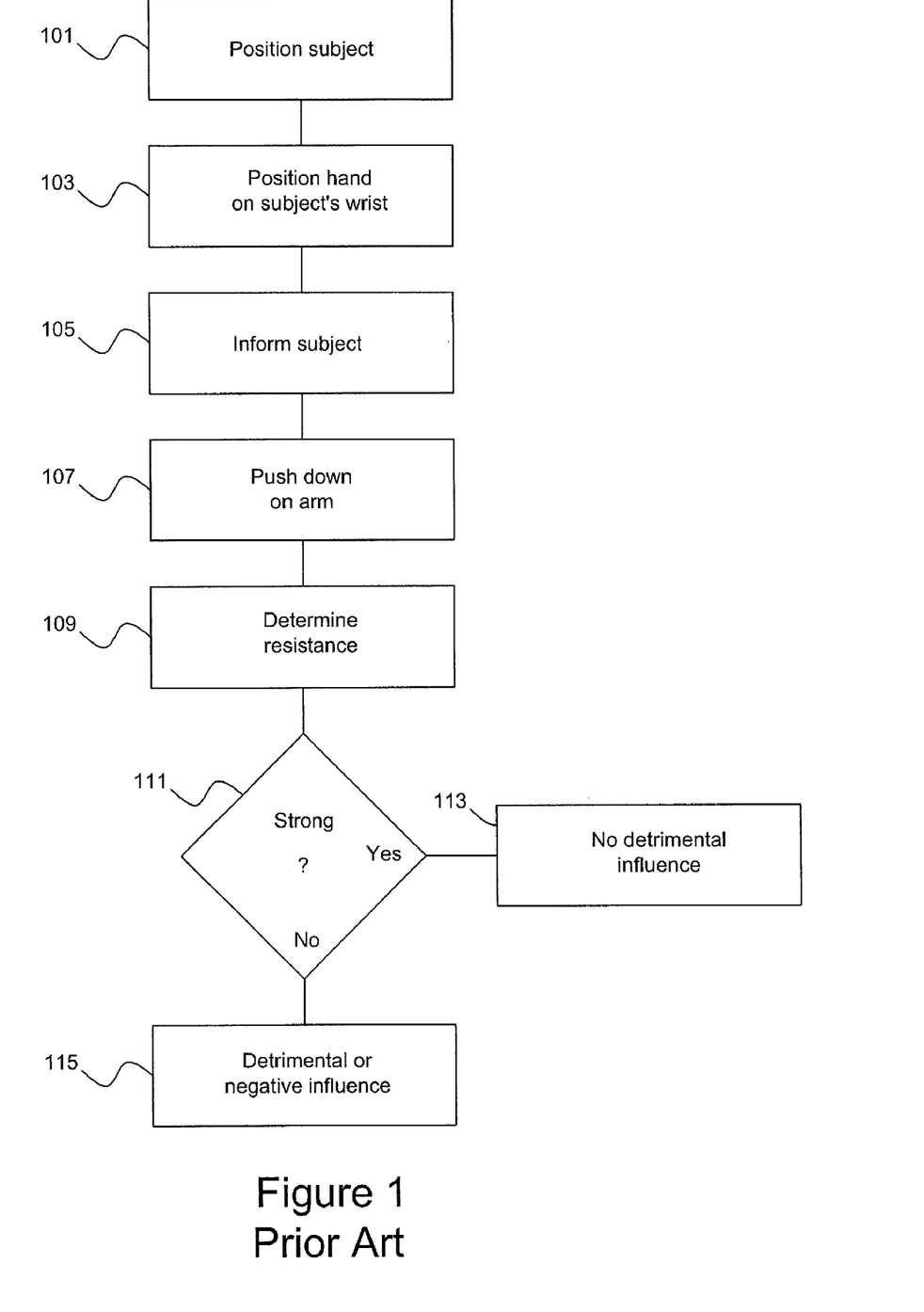
FIG. 1 is a flow diagram of a prior art kinesiology examination.

An example of a prior art kinesiology exam in FIG. 1 is taken from David Hawkins' "Power versus Force"1995, Veritas Publishing page 3, excerpted from H. O. Kendall's *Muscles: Testing and function* (Baltimore: Williams and Wilkins, second edition, 1971).

It takes two people to perform a kinesiological test. One is a friend or family member for testing. We'll call him or her, your subject, and you will be the examiner. Have the subject standing erect, right hand relaxed at subject's side, left arm held out parallel to the floor, elbow straight (Block 101). (You may use the other arm if you wish). Face your subject and place your left hand on his right shoulder to steady him. Then place your right hand on the subject's extended left arm just above the wrist (Block 103). Inform the subject you're going to try to push his arm down as he resists (Block 105). Now push down on his arm fairly quickly, firmly and evenly (Block 107). The idea is to push just hard enough to test this spring and balance in the arm but not so hard that the muscle becomes fatigued. The phenomenon is not a question of who is stronger, but of whether the muscle can "lock" the shoulder joint against the push. You then determine the resistance (Block 109) and determine whether it is strong or weak (Block 111).

Assuming there is no physical problem with the muscle and the subject is in a normal and relaxed state of mind, receiving no extraneous stimuli (for this reason it is important that the examiner not smile or otherwise interact with the subject), the muscle will "test strong"—that is the arm will remain locked or have a high resistance (Block 113). If the test is repeated in the presence of a negative stimulus (for instance, artificial sweetener), although you are pushing down no harder than before, the muscle will not be able to resist the pressure and the subject's arm will fall to his side (Block 115).

The same is the case for muscle responses to statements that are true and not true: the muscle staying strong under "true" conditions and going weak under "not true" conditions, (i.e., a false statement). Likewise, it has been reported by Davis, C. 2007 (in Hawkins, D. 2008 "Reality, Spirituality, and Modern Man) that the pupil dilates to false and constricts to true statements made by the individual. This smooth muscle, autonomic activity, provides a unique way of assessing the naturally occurring applied kinesiology response.

Goodhart (1976) also noted a response in individuals listening to statements of deceit; that is, large striated muscle tested weak in the presence of statements known to be false, such as the tape recordings of Lyndon Johnson talking about the "Tonkin gulf" or Edward Kennedy stonewalling on Chappaquiddick. These parsimonious observations by Goodhart carry implications for national security interests in that the false information is not being expressed by the individual tested (i.e., the person being tested isn't doing the lying), but the false information is being detected by the person listening to it. This particular phenomenon is described and explained by Hawkins as a "field effect". The theoretical explanation is in terms of quantum physics, "nonlocal effects", and hence somewhat "edgy" to the everyday understanding, but the observable functionality is what is remarkable and holds tremendous promise if the parameters by which it works are validated. In other words, because of the field effect of a false statement, one does not have to be present at the location to detect it.

An object of the present subject matter is to provide improved devices, systems, and methods for measuring characteristics of at least one eye, and particularly for measuring the physiological changes in the eyes under different conditions of truthfulness (beneficial) and falseness (non-beneficial).

Another object of the present subject matter is to remove subjective components of the muscle testing response from the testing individual by automatically monitoring an involuntary (autonomic) pupillary response using an automated process.

Yet another object of the present subject matter is to provide for a remote applied kinesiology examination.

These and many other objects and advantages of the present subject matter will be readily apparent to one skilled in the art to which the invention pertains from a perusal of the claims, the appended drawings, and the following detailed description of preferred embodiments.

DETAILED DESCRIPTION

Kinesiology glasses are a device that documents the phenomenon of the iris's response to truthfulness versus falseness (as well as beneficial versus non-beneficial conditions) and that gives immediate feedback to the individual. The device advantageously takes the subjective components of the muscle testing response out of the hands of the testing individual and monitors an involuntary (autonomic) pupillary response, using a photo/mechanical, computationally derived function effectively eliminating a subjective component to the muscle testing process while requiring only one individual be involved. The glasses may be a personalized, self-contained mechanism whereby an individual working solely by themselves can ascertain the results of the applied kinesiology response. In other words, an individual may obtain the truthfulness of a statement without the presence of a second person. Previous applied kinesiology responses required two individuals; an examiner and a subject. This device allows for self-evaluation and eliminates a subjective influence on obtaining the response between two people.

In one exemplary embodiment, self evaluation and elimination of subjective influences may be accomplished through a unique glasses-frame mounted device that is completely portable and self-contained. The glasses may also provide "truthfulness" information to the examiner on subjects or entities other than the testing individual. As applied kinesiology is based on a "field phenomenon" the subject of information is not limited to the individual using the device, and so, may have far-reaching applications for information gathering beyond the individual doing the testing.

The kinesiology glasses detect local pupillary response to truthfulness locally and remotely. An exemplary embodiment provides a measurement of pupil constriction or dilation over time to conditions of truthfulness or non-truthfulness, respectively (or conditions which are favorable or unfavorable physiologically to the individual, respectively) and provides sensory feedback to the individual wearing the device. Whereas the pupillary's surface area (and by direct operation diameter) response to truthfulness is a field phenomenon, remote assessment of truthfulness is possible. Exemplary embodiments are configured to measure pupil dilation in response to physiological conditions or truthful versus non-truthful statements.

Figure 2A:
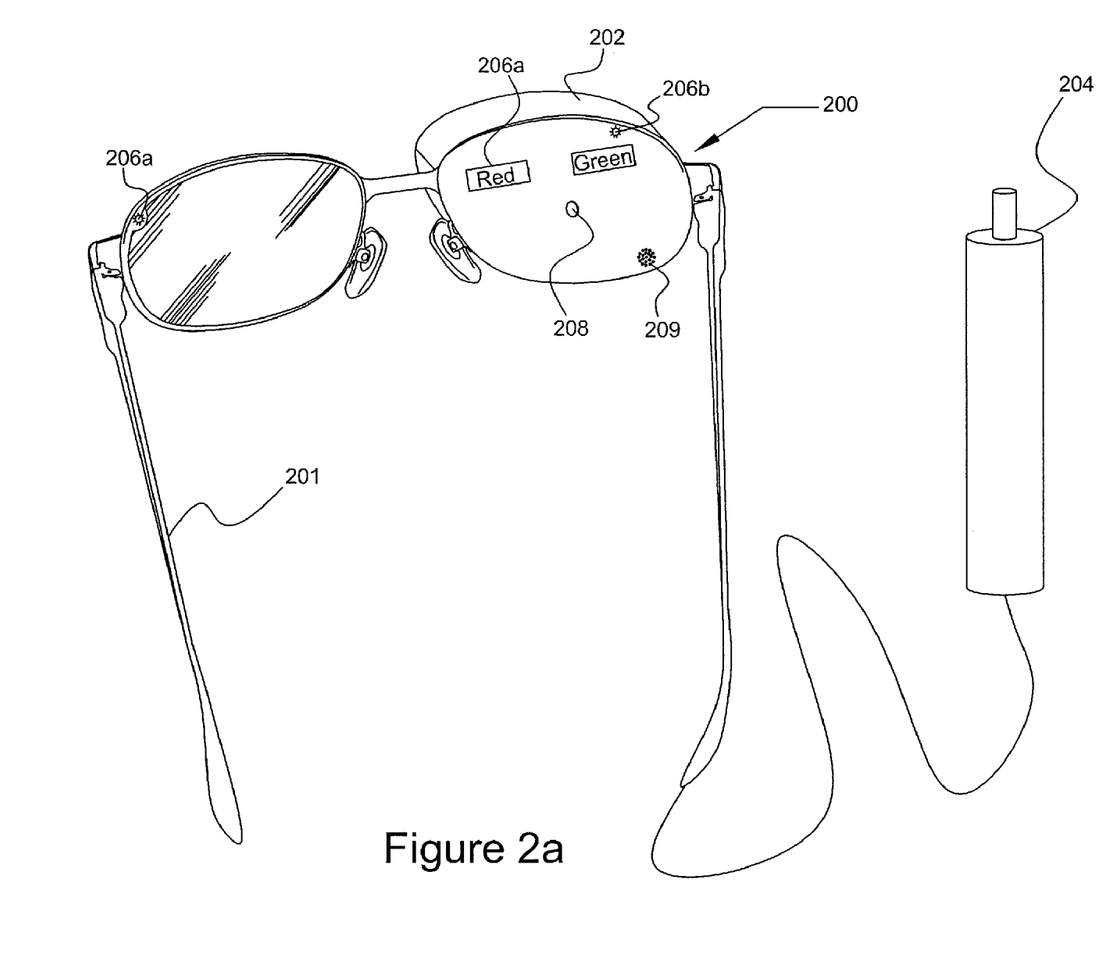
FIG. 2A is an illustration of applied kinesiology glasses according to an embodiment of the present subject matter.
Figure 2B:
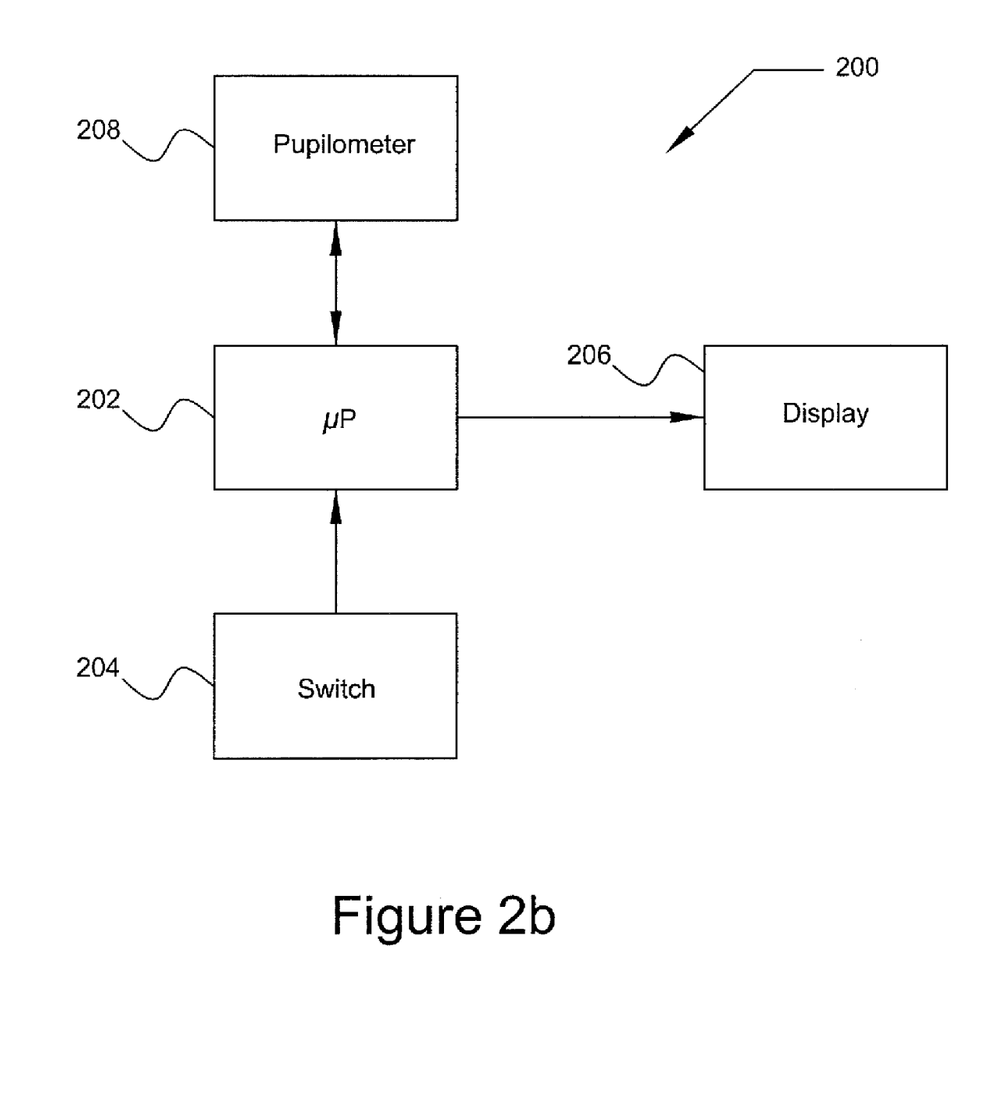
FIG. 2B is a schematic of applied kinesiology glasses according to an embodiment of the present subject matter.

FIGS. 2A and 2B illustrate an embodiment of the applied kinesiology glasses. A traditional eye glass frame 201 is shown which is adapted to serve as the applied kinesiology glasses. A pupil dilation sensor 208 that is capable of sensing the variations in the dilation of a subject's pupil is positioned within the eyeglass frame generally in the vicinity of the eyeglass lens so as to measure the dilation in the subject's pupil. Other locations which enable measurement of the pupil are also envisioned and anticipated. While in the figure, the right eye lens is shown as opaque, a transparent lens may well be used. A processor 202 may be integrated anywhere within the eyeglass frame 201 or may be external. In FIG. 2A, the processor 202 is positioned in the right lens area. A switch 204 is connected to the processor 202 and is capable of providing a signal indicating a transition (as will be later explained). In FIG. 2A, the switch 204 is shown as a hand held thumb activated switch connected to the eyeglass frame and the processor 202 via a flexible cord, the switch may also be voice activated employing a microphone 209 as part of the switch, to keep the examiner's hands free.

Two light emitting diodes 206a and 206b capable of providing an indication of at least one of a plurality of states and capable of observation by the subject are shown. In the embodiment of FIG. 2A; a red 206a (LED) indicates a false or negative state and a green 206b indicates a true or positive state. The state may also be indicated by a brightness of the LED, a cadence of the LED or a number of blinks of the LED, these latter types of indications are especially beneficial in designating states if only one LED is used. FIG. 2A also shows red and green displays (also labeled 206 a and b) or projections that may also be used to indicate a state. Liquid crystal display (LCD) may also be used to provide feedback.

As shown in FIG. 2B, the pupil dilation sensor 208 (pupilometer), which may be a digital camera, provides the processor 202 with information regarding the variation in pupil diameter (area). The processor 202 determines a control metric (normalized or base metric) based on the information received from the sensor 208 during the control period and determines a response metric based on the control metric and the additional information received from the sensor 208 during an active period. A pupilometer such as disclosed in U.S. Pat. No. 7,431,455, titled "Pupilometer for pupil center drift and pupil size measurements at differing viewing distances," the entirety of which is herein incorporated by reference, may be suitable for use as the pupil dilation sensor 208. The information provided by the sensor 208 may be digital images of the pupil and iris which may be processed by the processor 202 to determine the dilation of the pupil. The information may also be physical measurements of pupil or may be relative indicators of changes in the pupil's dilation. The sensor 208 may also include internal processing capabilities.

The processor 202 creates and sends control signals, based on the response metric and the base metric, or as described later may be based solely on the response metric. The control signals control the indicator 206 (display) in this embodiment causing the visual displays 206 or the red and green LEDs to turn on or off or otherwise indicate the state. The switch 204 controls and indicates the transition between the control period and the active (or response) period and is provided to the processor 202. In some embodiments the transition may be implied or assumed and thus the switch 204 may not be needed.

Figure 3:
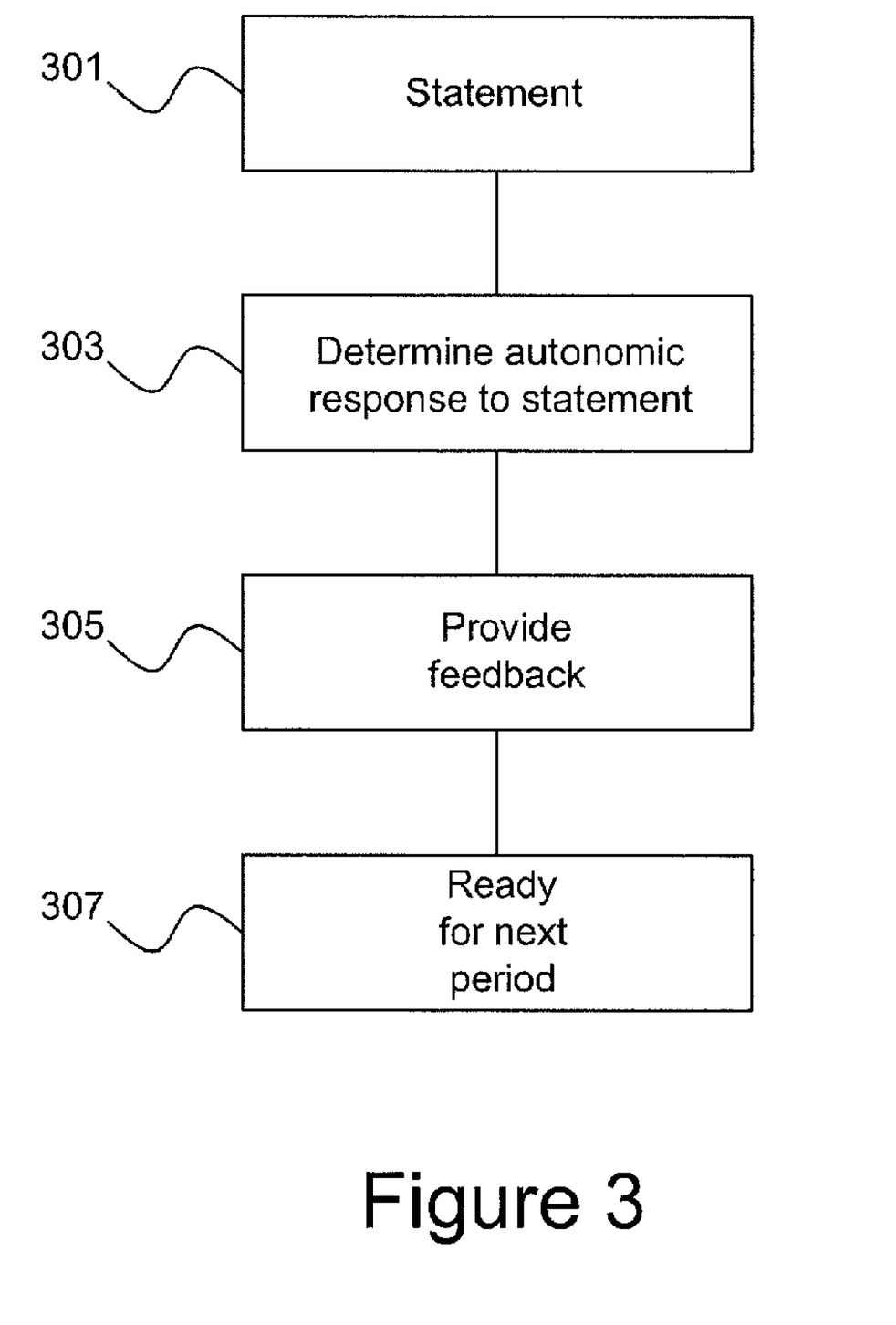
FIG. 3 is a flow diagram for a method of feedback delivery for an applied kinesiology exam according to an embodiment of the present subject matter.

FIG. 3 describes a method of providing an applied kinesiology exam with the kinesiology glasses upon transition.

1) A statement (stimulation) is made by the examiner as shown in Block 301.

2) The glasses' measuring process is activated as shown in Block 303. The activation may be by a verbal statement, i.e. "test" via a voice-activated switch, or may be by activating a mechanical switch, i.e. "a hand-held device". This process determines the autonomic response of the examiner to the statement.

3) The resultant increase (dilation) or decrease (constriction) in pupil size, as measured and determined by the device, triggers activation of either a red LED or green LED mounted on the interior of the glasses frame as shown in Block 305. This provides the examiner feedback information about whether the pupil has increased or decreased in size.

4) The device is then ready for another statement/pupil measuring period as shown in Block 307.

Figure 4:
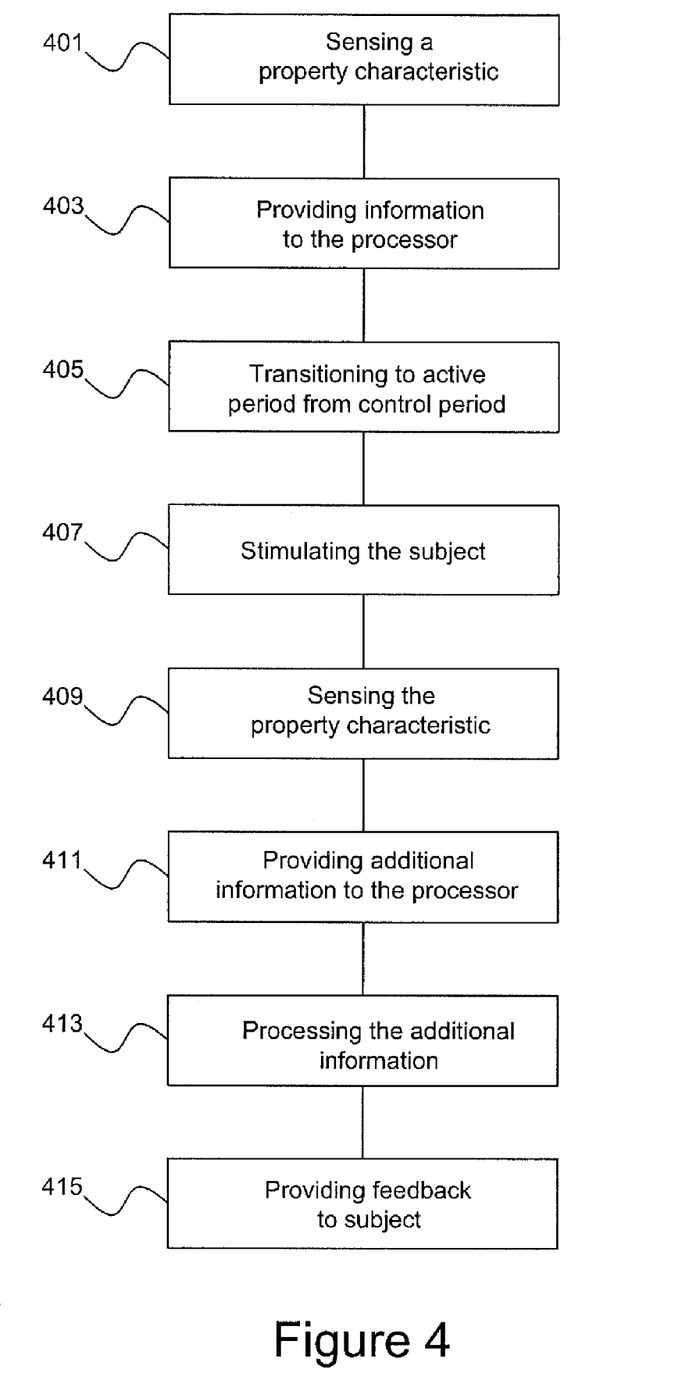
FIG. 4 is a flow chart for a method for obtaining applied kinesiology feedback.

FIG. 4 describes more specifically a method for obtaining applied kinesiology feedback. A property characteristic of a subject is sensed in Block 401 with a sensor. The property characteristic as noted above is preferably subject to autonomic variation. The property may also be selected from other autonomic responses such as body temperature, respiration rate, and/or psychophysiological effects. The psychophysiological effects may include measures of brain activity, such as brain waves (electroencephalography, EEG), fMRI (functional magnetic resonance imaging), measures of skin conductance (skin conductance response, SCR; galvanic skin response, GSR), cardiovascular measures (heart rate, HR; beats per minute, BPM; heart rate variability, HRV; vasomotor activity), muscle activity (electromyography, EMG), changes in pupil diameter with thought and emotion (pupillometry) and eye movements, recorded via the electro-oculogram (EOG) and direction-of-gaze methods. In Block 403 the information regarding the sensed property (pupil dilation) is communicated to the processor for processing. From this information, the processor may determine the baseline of the pupil diameter.

In Block 405 a transition is made from the control period to an active period; transition may be accomplished through the use of a switch, voice activation or manually. Alternatively, software may also analyze the changes in a property characteristic to determine a transition. For example a sharp deviation or a deviation above a predetermined threshold may be used as a pseudo real time transition to the active period. In another alternative, a base line may be established to compare all subsequent responses and the glasses remain in an active state. Simultaneously or in temporal proximity to the transition from the control period to the active period, the subject is stimulated to affect a response as shown in Block 407.

The property characteristic of the subject is sensed to obtain additional information regarding its autonomic response as shown in Block 409. The additional information regarding the sensed property characteristic is provided to the processor as shown in Block 411. The processor uses the additional information to determine the autonomic response during the active period as shown in Block 413. Feedback based on the autonomic response via the processor is provided to the subject as shown in Block 415. The feedback may be a visual signal including illuminating a light having a predetermined color to the subject, illuminating a light with a predetermined brightness to the subject, pulsing a blinking light at a predetermined frequency, or pulsing a light a predetermined number of pulses or combination thereof. The feedback may also be an aural signal such as a synthesized voice, a recorded voice, a tone, a volume or a number of audio pulses. The feedback may also be a non-audible vibration or other sensory stimulant.

Figure 5:
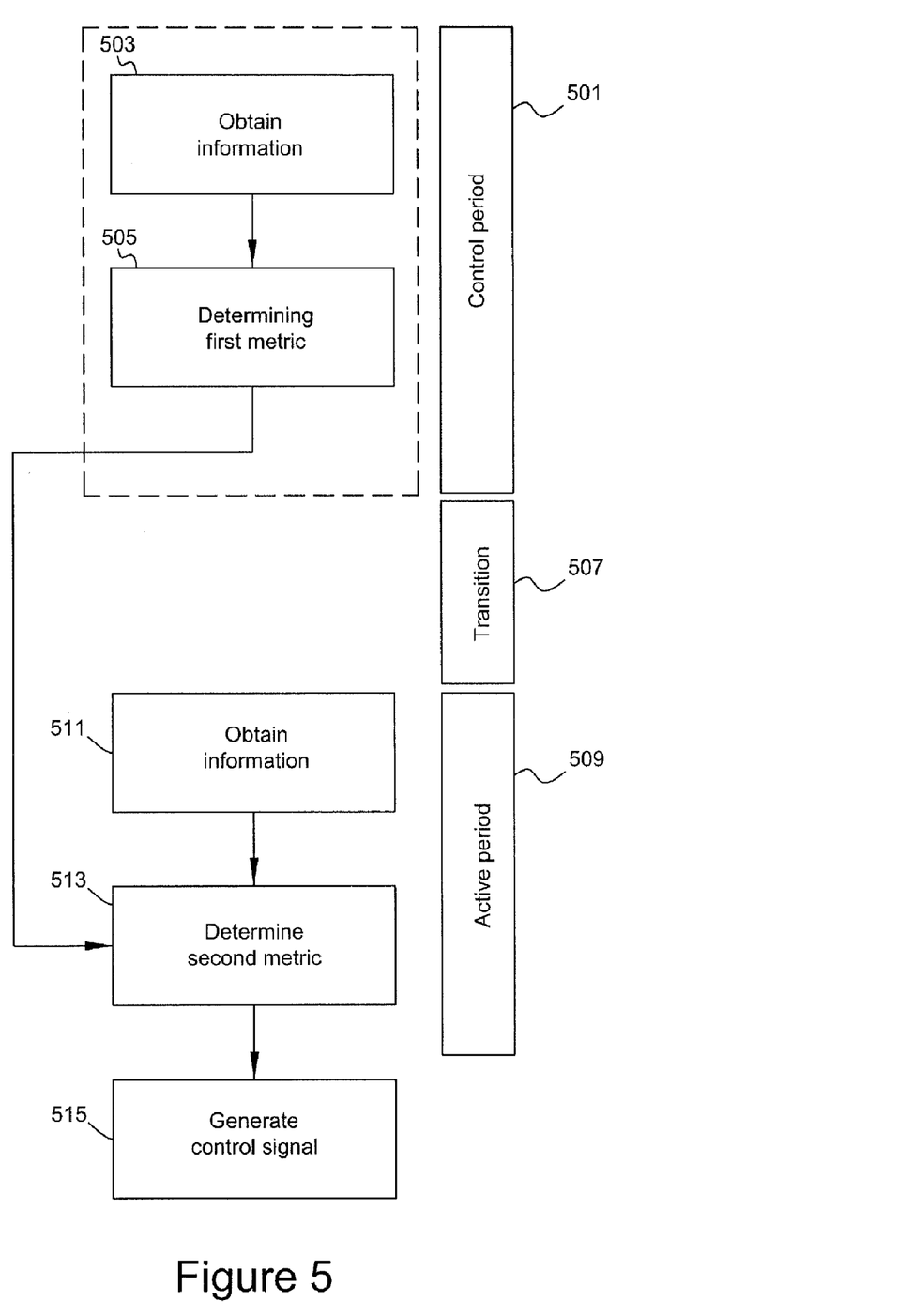
FIG. 5 is a flow diagram flow chart for determining the autonomic response in the pupil.

FIG. 5 is a flow chart for determining the autonomic response in the pupil. The characteristic of the pupil may be measured from the end point of the statement to the end of a specified time interval on a continuous basis. The resultant increase or decrease of the pupil characteristic, if beyond a certain predetermined criteria, triggers a positive feedback response or negative feedback response on the glasses (indicated by a green LED light or a red LED light, respectively).

The method for determining the autonomic response may be practiced covering three periods, the control period as shown in Block 501, the transition period as shown in Block 507 and the active (or response) period as shown in Block 509. As noted above the control period establishes a base line or normative value and expected deviations of the property characteristic (pupil dilation). The active or response period establishes the autonomic response temporal to the stimulus.

In Block 503 information is obtained on the diameter (area) of the pupil during the control period. The information may be an image or images of the pupil taken by a digital camera. This information is provided to a processor which determines a control metric (first metric) as shown in Block 505. For example from the images, the diameter, area, radius, etc. of the pupil may be determined and an average value or other statistical measure may be determined, such as a standard deviation to account for normal fluctuations in pupil size.

Subsequent to the transition period 507 additional information is obtained as shown in Block 511 during the active period 509. This information is reflective of the autonomic response. This information is provided to the processor which determines a response metric as shown in Block 513. The resulting changes (either increased or decreased, over time) calculations may then trigger either a red or green LED response mounted on the interior aspect of the lens' rim, depending on whether the response metric meets specific criteria. The response metric is determined based at least on the control metric and additional signals received from the digital camera during an active period. The images of the pupil from the response period may be used to determine an average value or other statistical measure; this value may then be compared to the control metric by mathematical or logical operation to arrive at a response metric. A control signal indicating the nature of the feedback may be generated based on the response metric as shown in Block 515.

For illustration purposes, the following example is provided. The initial sensing is done during a control period to obtain baseline information regarding the characteristic in a non-stimulated control period. In the embodiment described herein, the property characteristic is pupil diameter or dilation. During the control period a digital camera takes a series of five successive images of the subject's pupil. The five images show a pupil diameter of 2.1, 2.0, 1.9, 2.0 and 2.1 mm. The average diameter is 2.02 mm. The standard deviation is 0.08367. During the response period the digital camera takes another series of five images of the subject's pupil. The five images in the response period show a pupil diameter of 2.1, 2.1, 2.2, 2.1 and 2.2 mm. The average diameter is 2.14. A difference between the diameter averages is 0.12 mm (2.14−2.02=0.12 mm) The response metric may be as simple as this difference or may be a function of the difference, such as the difference divided by the standard deviation in which case the response metric could be 0.12/0.0837 or 1.43. Based on the positive response metric the processor would send a control signal to indicate a false or negative feedback. A −1.43 response metric in this example would result in the processor generating a control signal to indicative a true or positive feedback. A response metric less than 1 in this example may be ignored as it is within the standard deviation. However other statistics, metrics and thresholds may be used and the inclusion of this illustration is not exclusive, exhaustive or intended to be limiting.

Alternatively, upon a deviation in the pupil's characteristics, the transition to the active period can be assumed. A deviation in pupil characteristics as associated with a running average may be used to indicate a transition. As in the above example, the ten measurements taken are 2.1, 2.0, 1.9, 2.0, 2.1, 2.1, 2.1, 2.2, 2.1, and 2.2, a simple running metric of $$M = \frac{\frac{D_i + D_{i-1}}{2}}{\frac{2}{3}(D_{i-2} + D_{i-3} + D_{i-4})}$$

is calculated to detect non-spurious shifts in the pupil's characteristics. The running metric is calculated over a series of five successive measurements; at i=5 (the end of the control period) is 1.025, at i=6 is 1.07 and at i=7 is 1.05 and at i=8 is 1.04. The local peak of 1.07 reveals the dilation of the pupil and transition to the response period, likewise a local dip in the running metric reveals constriction of the pupil and a transition. Other method or algorithms for assuming the transition are also envisioned.

Figure 6:
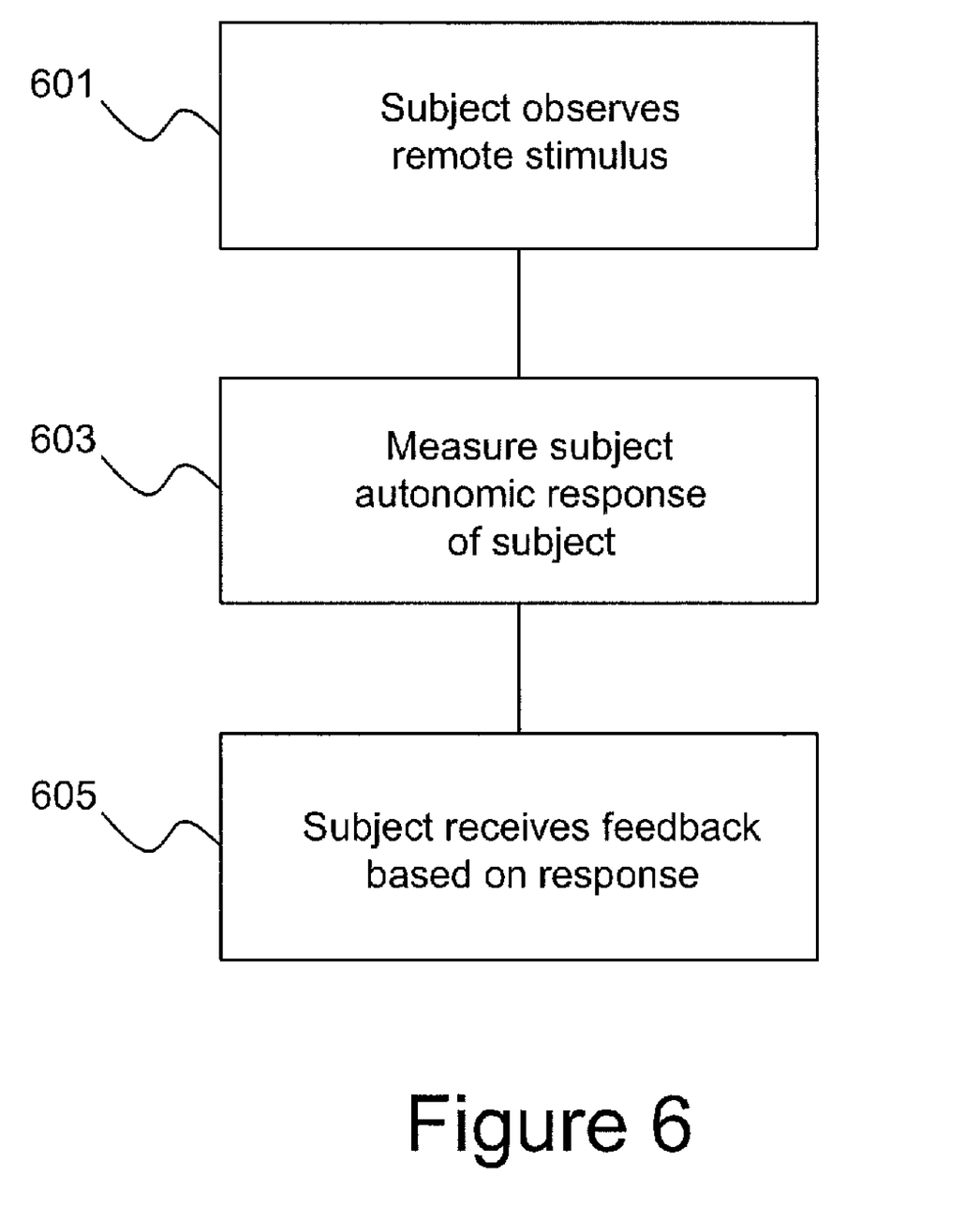
FIG. 6 is a flow chart of a method for obtaining applied kinesiology feedback remotely.

FIG. 6 is a flow chart of a method for obtaining applied kinesiology feedback remotely. First the subject observes the remote stimulus as shown in Block 601. The observation may be visual or aural and may be in real time, i.e. a live video or audio feed or may be prerecorded. The autonomic response of the subject is measured as shown in Block 603 and based upon the response, feedback indicating the truthfulness or falseness of the observed behavior is generated as shown in Block 605. For example an interrogation of a suspect is captured on a live video feed. The applied kinesiology examiner wearing the applied kinesiology glasses observes the interrogation and from measurements of the examiner's (not the suspect's) pupil dilation in response to the interrogation, the truthfulness or falseness of the suspect's statement may be objectively determined.

An advantage of the applied kinesiology glasses is to provide a simple and unique means of delivering feedback on the applied kinesiology response of the pupil. The glasses provide visual or other form of feedback of a true versus not true response to a particular statement or stimulus. As noted above this may advantageously be done by an apparatus built into the frame of glasses that measures the area of the pupil as it dilates or constricts to a particular statement. Additionally, the processing and feedback indication may be done external to the glasses such as by a laptop computer connected by tether or wirelessly to the glasses.

Aspects of the present subject matter include the determination of a true state, a false state and an indeterminate state.

Another aspect of this device which is unique is that it captures the pupillary response to a given stimulus (a particular statement) (triggered by either a voice activated signal or a mechanical signal) and feeds back that information to the individual in an expeditious, fourth right manner. The application of the glasses is to eliminate a subjective component of muscle testing which relies on striated/voluntary muscles and provide an alternate means of assessing the applied kinesiology response with an involuntary (non-volitional) objective measure derived through a unique device measuring iris movement (constriction or dilation of the pupil).

Yet another aspect of the present subject matter is it allows the individual to test themselves for diagnostic purposes (eliminating the need for another practitioner) and allows diagnostic processes to be done on other individuals without them being present. This allows for portability, convenience, and eliminates subjectivity that may be involved with an additional individual. In addition to the diagnostic implications, the glasses represent a step forward in the ability and means to make assessment decisions (true versus false) in a remote manner. Implications for the disclosed subject matter are far-reaching including medical assessment and diagnosis, lie detection, armed service conditioning, gaming and remote/distant knowledge gathering through a convenient and non-intrusive, and individualized, method and apparatus.

Aspects of the disclosed subject matter may be specifically implemented by algorithms embedded in software or application specific integrated circuits (ASIC).

While preferred embodiments of the present invention have been described, it is to be understood that the embodiments described are illustrative only and that the scope of the invention is to be defined solely by the appended claims when accorded a full range of equivalence, many variations and modifications naturally occurring to those of skill in the art from a perusal hereof.

I claim:

1. Applied kinesiology feedback glasses comprising:
an eye glass frame;
a pupil dilation sensor capable of sensing the variations in the size of a subject's pupil;
said pupil dilation sensor attached to the eye glass frame;
a processor;
a switch; said switch connected to the processor and providing a signal indicating at least a transition between a control period and an active period;
at least one light emitting diode capable of providing an indication of at least one of a plurality of states and said indication observable by the subject when said pupil dilation sensor is positioned to sense the variations in the size of the subjects pupil; said indication selected from the group consisting of a color of the (LED), a brightness of the LED, a cadence of the LED and a number of blinks of the LED;
said pupil dilation sensor providing the processor with information regarding the variation in pupil size and said processor capable of determining a metric based on plural information received from the sensor during a control period and capable of determining a second metric based at least on the first metric and additional information received from the sensor during an active period, said processor creating a control signal based on the second metric; said control signal causing said at least one light emitting diode said indicator to display the indication of one of at least one of the plurality of states.

2. The glasses of claim 1, wherein the plurality of states are selected from the group consisting of true, false and undetermined.

3. The glasses of claim 1, wherein the pupil sensor comprises a digital camera, wherein the information regarding the variation in pupil diameter are images of the pupil and iris.

4. An applied kinesiology feedback device comprising:
a property sensor capable of sensing a property characteristic of a subject, said property characteristic subject to autonomic variation;
a processor;
a feedback indicator; and,
a cycle signal designating one of a control period and an active period;
said property sensor at least in one way communication with the processor, wherein signals representative of the subject's property characteristic and the cycle signal are received and processed by the processor;
wherein said processor having operable control of the feedback indicator; said feedback indicator, in response to a control signal from the processor, presents an indication of at least one of a plurality of states; and, wherein the indication is observable by subject when the property sensor is in a position to sense the property characteristic of the subject.

5. The device of claim 4, wherein the property characteristic is selected from the group consisting of pupil diameter, temperature, respiration rate, psychophysiological effects and muscle response.

6. The device of claim 4, wherein the property sensor is selected from the group consisting of a pupilometer, an ohmmeter, a strain gage, a thermometer, an EEG, an EOG, an EMG a fMRT and a digital camera.

7. The device of claim 4, wherein the indicator is visual.

8. The device of claim 7, wherein the indication is selected from the group consisting of a color, brightness, a cadence, and a number of pulses.

9. The device of claim 4, wherein the indicator is aural.

10. The device of claim 9, wherein the indication is selected from the group consisting of a synthesized voice, a recorded voice, a tone, a volume, a number of pulses and a low frequency vibration.

11. The device of claim 4, wherein the property sensor is a digital camera, the property characteristic is pupil diameter and the signals representative of the property characteristics are images of the pupil and iris; wherein the processor is capable of determining a metric based on the signals received from the digital camera and the cycle signal.

12. The device of claim 4, wherein the property sensor is a digital camera, the property characteristic is pupil diameter and the signals representative of the property characteristics are images of the pupil and iris; wherein the processor is capable of determining a metric based on the signals received from the digital camera during the control period and capable of determining a second metric based at least on the first metric and additional signals received from the digital camera during an active period, said processor creating a control signal based on the second metric; said control signal causing said indicator to display an indication of the at least one of the plurality of states.

13. The device of claim 12, wherein the first metric is an average of the pupil diameter measured during the control period and the second metric is related to the pupil diameter during the active period.

14. The device of claim 13, wherein the second metric is an average or a derivative thereof.

15. The device of claim 12, wherein the second metric is compared to a predetermined threshold.

16. A method of feedback delivery for an applied kinesiology exam comprising;
sensing a property characteristic of a subject with a sensor during a control period to obtain information, wherein said property characteristic subject to autonomic variation;
providing the information regarding the sensed property characteristic to a processor for processing;
transitioning from a control period to an active period;
stimulating the subject to illicit a response;
sensing the property characteristic of the subject to obtain additional information;
providing the addition information regarding the sensed property characteristic during the active period to the processor;
processing the additional information to determine a response of the property characteristic to the stimulation; and,
providing feedback determined by the processor to the subject during the applied kinesiology exam based on the determined response.

17. The method of claim 16, where the step of providing feedback includes at least providing a visual signal.

18. The method of claim 17, wherein the visual signal is selected from the group consisting of illuminating a light having a predetermined color to the subject, illuminating a light with a predetermined brightness to the subject, pulsing a blinking light at a predetermined frequency, and pulsing a light a predetermined number of pulses.

19. The method of claim 16, wherein the step of providing feedback includes at least providing an aural signal.

20. The method of claim 18, wherein the aural signal is selected from the group consisting of a synthesized voice, a recorded voice, a tone, a volume, a number of pulses and a low frequency vibration.

21. The method of claim 16, wherein the property sensor is a digital camera, the property characteristic is pupil diameter and the signals representative of the property characteristics are images of the pupil and iris; wherein the processor is capable of determining an metric based on the signals received from the digital camera during the control period and a capable of determining a second metric based at least on the first metric and additional signals received from the digital camera during an active period, said processor creating a control signal based on the second metric; said control signal causing said indicator to display an indication of the at least one of the plurality of states.

22. The method of claim 16, wherein the stimulus is a true or false statement.

* * * * *